000

(12) United States Patent
Ahari

(10) Patent No.: US 9,179,999 B2
(45) Date of Patent: Nov. 10, 2015

(54) APPARATUS AND METHOD FOR INSTALLING A STENT

(71) Applicant: MED-Genesis, LLC, Clearwater, FL (US)

(72) Inventor: Frederick Ahari, Belleair Beach, FL (US)

(73) Assignee: MED-Genesis, LLC, Clearwater, FL (US)

( * ) Notice: Subject to any disclaimer, the term of this patent is extended or adjusted under 35 U.S.C. 154(b) by 258 days.

(21) Appl. No.: 13/911,469

(22) Filed: Jun. 6, 2013

(65) Prior Publication Data

US 2014/0364929 A1    Dec. 11, 2014

(51) Int. Cl.
*A61F 2/06* (2013.01)
*A61F 2/07* (2013.01)
*A61F 2/954* (2013.01)

(52) U.S. Cl.
CPC . *A61F 2/07* (2013.01); *A61F 2/954* (2013.01); *A61F 2002/065* (2013.01); *A61F 2002/067* (2013.01)

(58) Field of Classification Search
CPC .............. A61F 2/06; A61F 2/07; A61F 2/86; A61F 2/95; A61F 2/954; A61F 2002/065; A61F 2002/067; A61F 2250/0037
See application file for complete search history.

(56) References Cited

U.S. PATENT DOCUMENTS

| | | | |
|---|---|---|---|
| 6,264,662 B1 * | 7/2001 | Lauterjung | 606/108 |
| 6,270,464 B1 | 8/2001 | Fulton, III et al. | |
| 2004/0002714 A1 * | 1/2004 | Weiss | 606/108 |
| 2005/0182476 A1 * | 8/2005 | Hartley et al. | 623/1.11 |
| 2006/0178733 A1 * | 8/2006 | Pinchuk et al. | 623/1.35 |
| 2007/0299498 A1 * | 12/2007 | Perez et al. | 623/1.11 |
| 2008/0288045 A1 * | 11/2008 | Saeed | 623/1.14 |
| 2009/0005851 A1 * | 1/2009 | Pamoukian | 623/1.11 |

* cited by examiner

*Primary Examiner* — Jonathan W Miles
*Assistant Examiner* — Todd J Scherbel
(74) *Attorney, Agent, or Firm* — Nilay J. Choksi; Ronald E. Smith; Smith & Hopen, P.A.

(57) ABSTRACT

A method for installing a stent graft in therapeutic relation to an abdominal artery aneurysm includes the steps of advancing the stent graft over a guide wire and an introducer sheath, followed by advancing a main catheter over the guide wire and the introducer sheath. An inner catheter in the lumen of the main catheter is pulled to cause a magnet-carrying extended arm to encounter a kick plate in the main catheter lumen and to exit that lumen through an exit opening formed in the main catheter. A mating catheter having a magnetic tip is advanced over a contralateral guide wire and manipulated until the respective magnets engage. After specific positioning of the contralateral guide wire, the magnets are decoupled, the mating catheter is retracted, the inner catheter is pushed to return the extended arm into the main catheter lumen through the exit opening and the main catheter is withdrawn.

18 Claims, 17 Drawing Sheets

APPARATUS AND METHOD FOR INSTALLING A STENT

BACKGROUND OF THE INVENTION

1. Field of the Invention

This invention relates to surgical tools and methods. More specifically, it relates to a tool and method for installing a stent graft in an abdominal artery to prevent rupturing of the artery due to an aneurysm.

2. Brief Description of the Related Art

When stents for the abdominal artery were first introduced, the patient's torso was opened in a major operation, known as abdominal aortic aneurysm (AAA) repair. The abdominal artery lies in front of the spine but behind the major organs, several of which had to be moved out of the way so that the stent graft could be installed. Accordingly, AAA surgery could last six to eight hours, and was followed by a long and painful recovery period.

Modern stent grafts, however, are introduced into the abdominal artery through a small incision made in each of the common iliac arteries, thereby avoiding the complications often associated with AAA and greatly reducing the time required to complete the operation, post-operative pain and recovery time.

Since the patient's torso is not opened, the stent graft and the tool or tools used to position it in the desired position must be viewed through suitable imaging means.

The placement of guide wires and catheters needed to control stent graft placement can be difficult. In a worst-case scenario, the placement procedure may not work and the surgeon must resort to conventional AAA.

Thus there is a need for an improved tool and method for installing a stent graft in therapeutic relation to a diseased section of an abdominal artery. The improved tool and method would simplify stent graft placement and reduce the number of times that minimally invasive surgery must be abandoned in favor of prior art surgery.

However, in view of the art considered as a whole at the time the present invention was made, it was not obvious to those of ordinary skill in the field of this invention how such an improved tool and method could be provided.

BRIEF SUMMARY OF THE INVENTION

The long-standing but heretofore unfulfilled need for an improved tool for installing a stent graft in a diseased artery and a method for its use is now met by a new, useful, and nonobvious invention.

The novel structure has utility in facilitating the installation of a stent graft having an elongate limb and a truncate limb in an abdominal artery for treatment of an abdominal aortic aneurysm.

The novel method includes the now conventional step of advancing a main body of the stent graft over a main body guide wire and a first introducer sheath to deliver and deploy the main body where needed without blocking the renal arteries. This insertion is made through a first common iliac artery.

The term "proximal" as used hereinafter is defined as the end of the guide wire, catheter, cannula, or other mechanical structure that is nearest to the surgeon. The term "distal" will therefore refer to the end furthest from the surgeon. The alternative definition where "proximal" refers to nearest the heart and "distal" refers to furthest from the heart is not used.

The novel structure includes a main catheter having a non-round lumen that houses an inner cannula. The inner cannula is slideably received within the non-round lumen of the main catheter and can be pushed by a surgeon in a proximal-to-distal direction or pulled by the surgeon in a distal-to-proximal direction.

The inner cannula is defined as a first cannula that slideably receives a main guide wire and a second cannula that includes an extended arm. However, in a second embodiment, the extended arm is the only part of the second cannula.

The lumen is oval or some other suitable non-round shape to prevent relative rotation between the inner cannula and the main catheter. Accordingly, rotation of the main catheter about its longitudinal axis of symmetry effects simultaneous and corresponding rotation of the inner cannula.

The inner cannula is non-round because it is formed by first and second parallel cannulas that are secured to one another at their respective distal ends. A first cannula is dedicated to slideably receiving a main guide wire as aforesaid and a second cannula provides an extended arm that, like the main guide wire, has utility in placement of the stent graft. In end view or transverse section the first and second cannulas produce a figure eight profile.

The first and second cannulas are provided in two (2) embodiments but they are interconnected to one another at their respective distal ends in both embodiments.

In the first embodiment, the first and second cannulas are secured to one another at their respective distal ends and also along their respective lengths. The second cannula is cut a few inches from its distal end and is separated from the first cannula from the cut to the point where its distal end is connected to the distal end of the first cannula.

In the second embodiment, the first and second inner cannulas are not secured to one another along their respective lengths proximal to the interconnected distal ends.

In the second embodiment, an extended arm is formed by cutting the second cannula a few inches proximal to its distal end and discarding the extent of said second cannula that is proximal to the cut. The distal end of the extended arm is thus secured to the distal end of the first cannula, it being understood that the extended arm is the preserved, not discarded length of the second cannula.

In both embodiments of the inner cannula, an exit opening is formed in the main catheter so that the free end of the extended arm exits and re-enters the exit opening as the steps of the novel method are followed. In a first embodiment of the extended arm, the free end or tip of the extended arm has a ferromagnetic material, i.e., a metallic wire extending from said extended arm for a short distance. In a second embodiment of the extended arm, a magnet supplants the wire.

The operator advances and rotates the main catheter so that the exit opening and the extended arm are positioned in alignment with the gate of the stent graft, said gate being positioned in the truncate limb just below the flow divider of the stent graft as is well-known.

The main catheter is then advanced over the main body guide wire and the first introducer sheath until a leading end of the main catheter is positioned distal to the distal end of the stent graft. The operator then manually pulls the inner cannula in a distal-to-proximal direction, i.e., the inner cannula is retracted relative to the main catheter to allow the extended arm of the inner cannula to advance out of the main catheter exit opening. A kick plate is provided as a part of the main catheter for that purpose, i.e., the extended arm encounters the kick plate as the inner cannula is retracted and said kick plate directs the free end of the extended arm to exit the main catheter through the exit opening.

The main catheter is then manipulated until the free end of the extended arm is external to the truncate limb of the stent graft, i.e., until the free end of the extended arm has passed through the gate of the stent graft and exited the truncate limb.

A mating catheter has an exit opening formed in it as well and has a magnetic tip secured to its distal end. The mating catheter is advanced over a contralateral guide wire introduced through the second common iliac artery and a second introducer sheath smaller in diameter than the first introducer sheath is introduced through said second common iliac artery.

In the first embodiment of the extended arm, the operator advances the mating catheter and manipulates it until the magnetic tip of the mating catheter magnetically couples with the ferromagnetic material at the tip of the extended arm. In the second embodiment of the extended arm, the operator advances the mating catheter and manipulates it until the magnetic tip of the mating catheter magnetically couples with the magnetic tip of the extended arm, said magnetic tips being of opposite polarity.

The main catheter and the mating catheter are then advanced together in a proximal-to-distal direction through the gate in order to advance the contralateral guide wire through an exit opening formed in the mating catheter. The contralateral guide wire is advanced until it is distal of the distal end of the stent graft as is the main guide wire. The gate is thus said to be cannulated.

The magnetically engaged tips are then decoupled from one another by holding the main catheter in a fixed position while pulling on the mating catheter.

The mating catheter is then retracted through a contralateral puncture site, leaving the contralateral guide wire in place.

The inner cannula is then pushed in a proximal-to-distal direction to retrieve the extended arm into the main catheter through the exit opening formed in the main catheter. The main catheter is then withdrawn in a distal-to-proximal direction through the puncture opening formed in the ipsilateral side of the patient's body, leaving the main catheter guide wire and the contralateral guide wire in place.

The contralateral wire is then used to advance the contralateral stent graft limb until it is accurately placed.

The novel structure further includes a radiopaque ring that is positioned in the lumen of the main catheter. The radiopaque ring has an opening formed therein that is in registration with the exit opening formed in the main catheter. The radiopaque ring enhances the imaging of the main catheter exit opening location and structurally reinforces the main catheter in the region of the main catheter exit opening.

The radiopaque ring further includes a kick plate that controls an angle of exit of the extended arm from the main catheter.

An important object of the invention is to simplify the procedure required to install a stent graft in a diseased abdominal artery;

A closely related object is to facilitate gate cannulation, i.e., to facilitate the introduction of a contralateral guide wire into the gate of the stent graft;

A broad object is to provide improved tools that enable the procedures of stent graft introduction and placement to be simplified; and Another object is to provide a means for magnetically coupling together the free end of an extended arm that forms a part of an inner cannula and the free end of a mating catheter.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
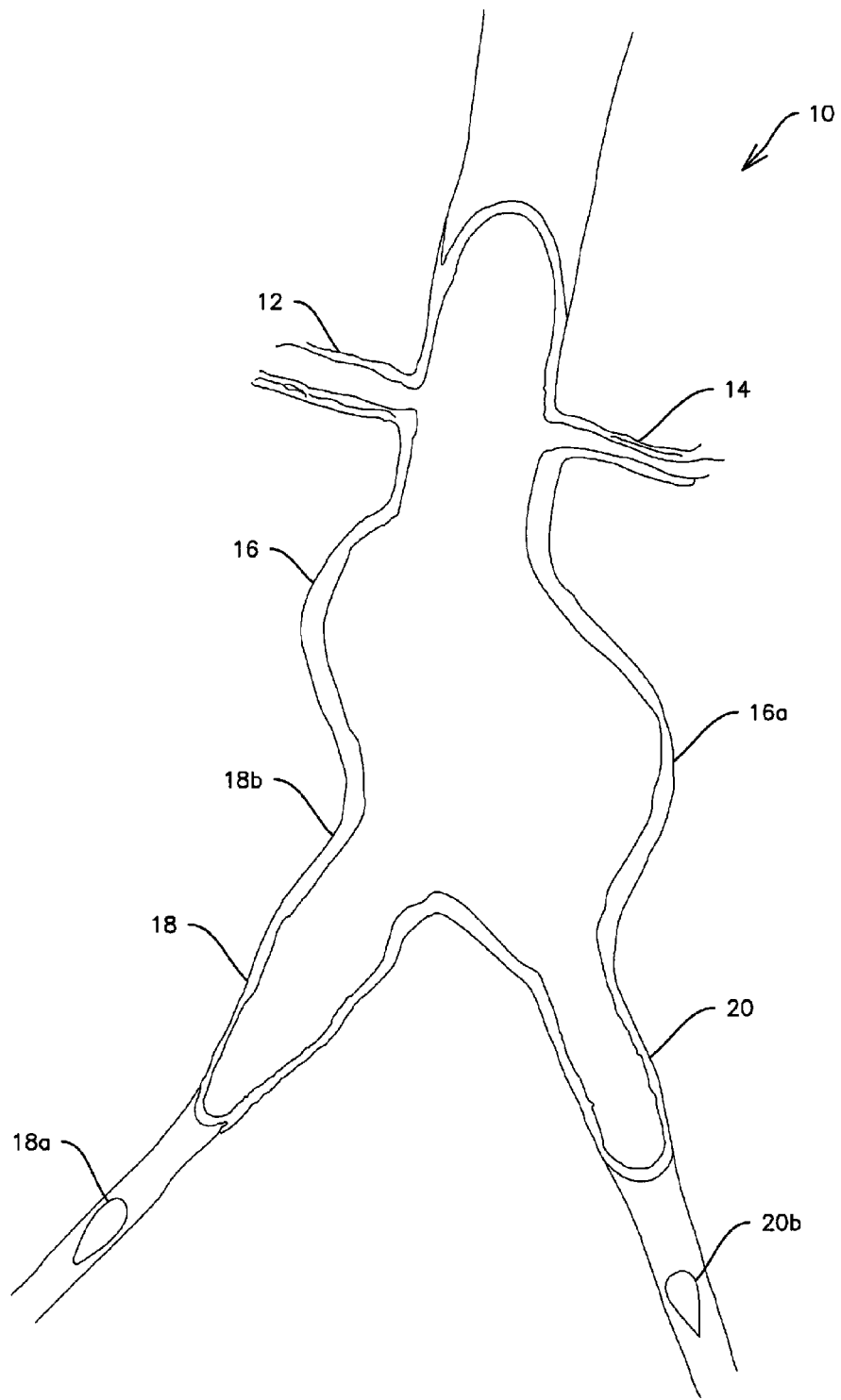
FIG. 1 is a diagrammatic representation of the renal, abdominal, femoral and iliac arteries where the abdominal and iliac arteries are diseased.

A system of renal, abdominal, and iliac arteries is denoted in FIG. 1 as a whole by the reference numeral 10. Healthy renal arteries are denoted 12, 14, an abdominal artery having a diseased section 16a where an aneurysm has formed is denoted 16, a first common iliac artery having a diseased section 18b where an aneurysm has formed is denoted 18, and a second, healthy common iliac artery is denoted 20. 18a indicates where first common iliac artery 18 is cut down for insertion of guide wires, insertion sheaths, and catheters, and 20a indicates where second common iliac artery 20 is cut down for the same reason.

Figure 2:
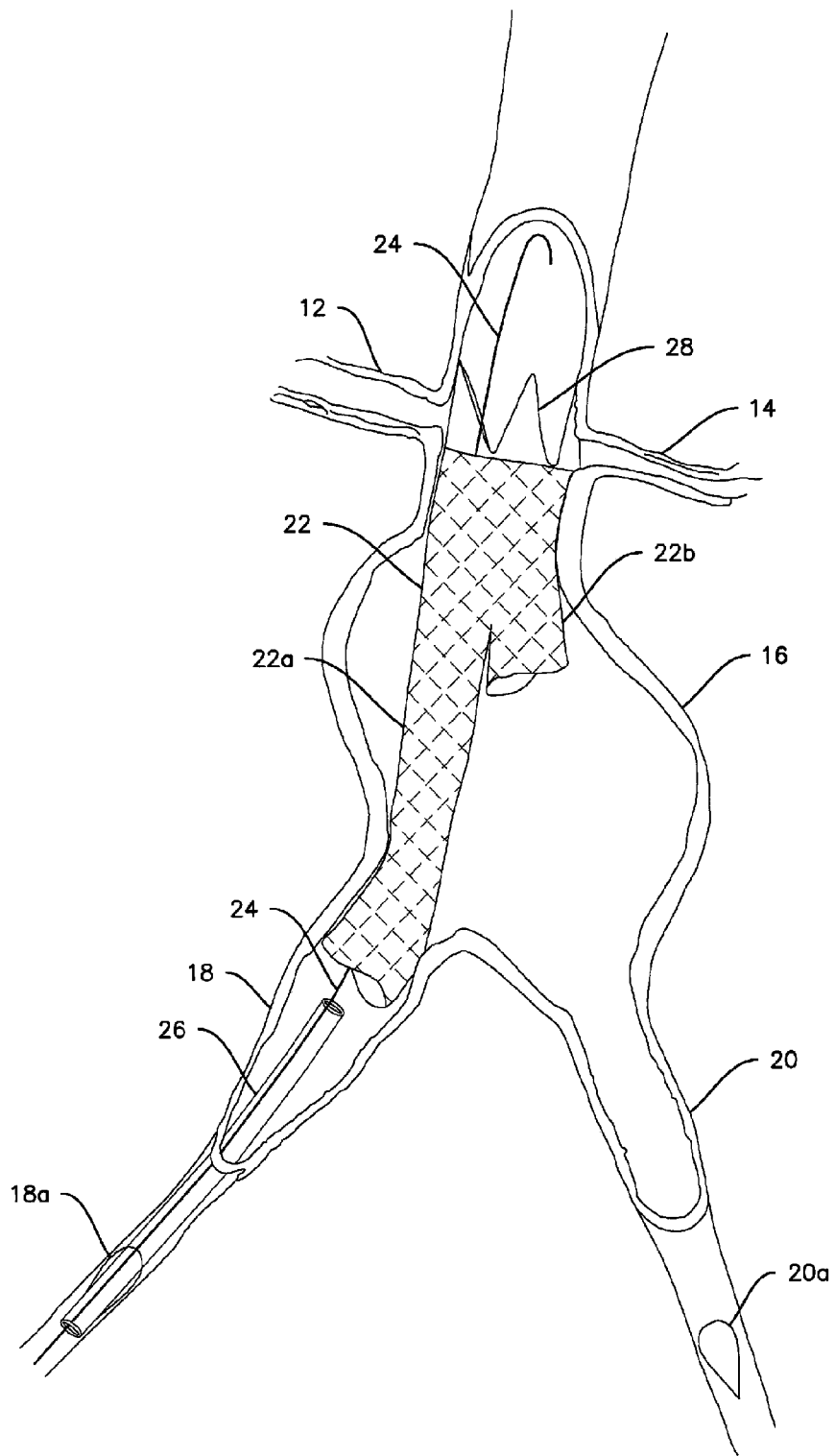
FIG. 2 is the first animation in a series of eleven (11) animations depicting how the abdominal aneurysm of FIG. 1 is treated with a stent graft.

FIG. 2 depicts arterial system 10 when the main body of stent graft 22 is advanced over guide wire 24 and introducer sheath 26. The delivery system used to deliver and deploy the main body of a stent graft is not depicted; FIG. 2 is a post deployment depiction.

Stent graft 22 has elongate limb 22a and truncate limb 22b and is deployed so that it does not interfere with renal arteries 12, 14. Wires 28 are known in the industry as the bare stent because no graft covers the bare wires. Wires 28 have no significant effect on blood flow through said renal arteries. In FIG. 2, guide wire 24 and introducer sheath 26 are in position for advancing a novel main catheter, not depicted in FIG. 2.

Figure 3:
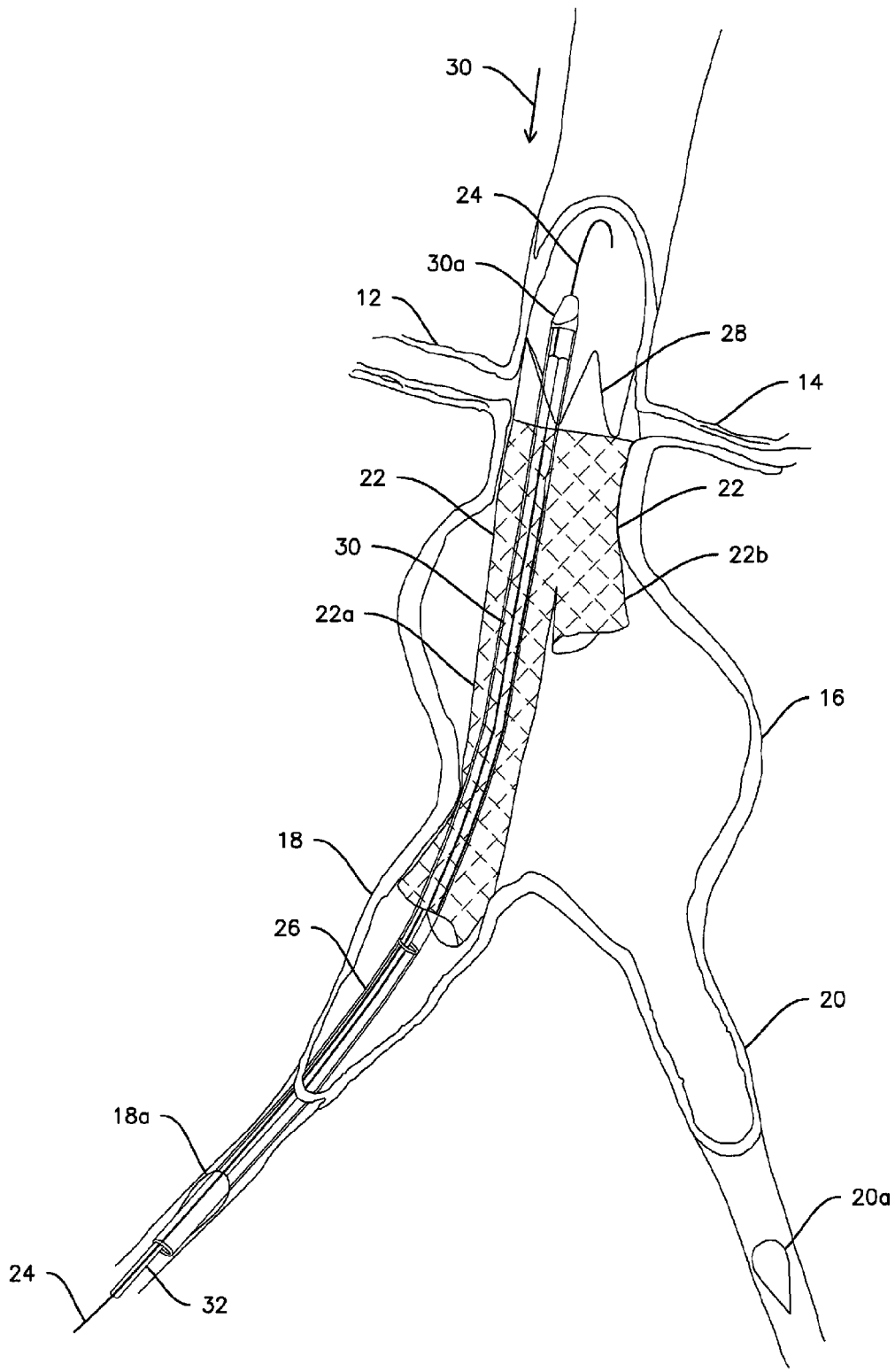
FIG. 3 is the second animation of said series of animations.

As depicted in FIG. 3, novel main catheter 30, having exit opening 31 formed therein, is then advanced over guide wire 24 and introducer sheath 26 until leading or distal end 30a of said main catheter is positioned beyond the distal end of stent graft 22. Distal end 30a is clearly visible under fluoroscopic imaging.

Reference numeral 32 at the lower left corner of FIG. 3 indicates the inner cannula that is slideably mounted within the non-round lumen of main catheter 30. The lumen of the main catheter may be round, like the external surface of the main catheter, if the inner cannula extends through a non-round structure that is added to the round lumen. One example of a non-round lumen is denoted 29 in FIG. 13B.

Inner cannula 32 is formed by two cannulas that are secured to one another at their respective distal ends.

In a first embodiment of the inner cannula, the two cannulas are secured to one another along their respective lengths, thereby forming a figure eight configuration in transverse section or end view. The second cannula is cut a few inches from its distal end and separated from the first cannula along those few inches except at its distal end which is joined to the distal end of the first cannula.

In a second embodiment of the inner cannula, the two cannulas are not secured to one another along their respective lengths proximal to the interconnected distal ends. In this second embodiment, the second cannula is cut a few inches from its distal end and the extent of the cannula proximal to the cut is discarded. The remaining extent of the second cannula forms the extended arm.

The two cannulas that collectively form the inner cannula are joined to one another at their respective distal ends in both embodiments. First cannula 32a of said two cannulas slideably receives guide wire 24 and second cannula 32b forms extended arm 36. Extended arm 36 is held against first inner cannula 32a by main catheter 30 when extended arm 36 is disposed within the lumen of main cannula 30.

Figure 4:
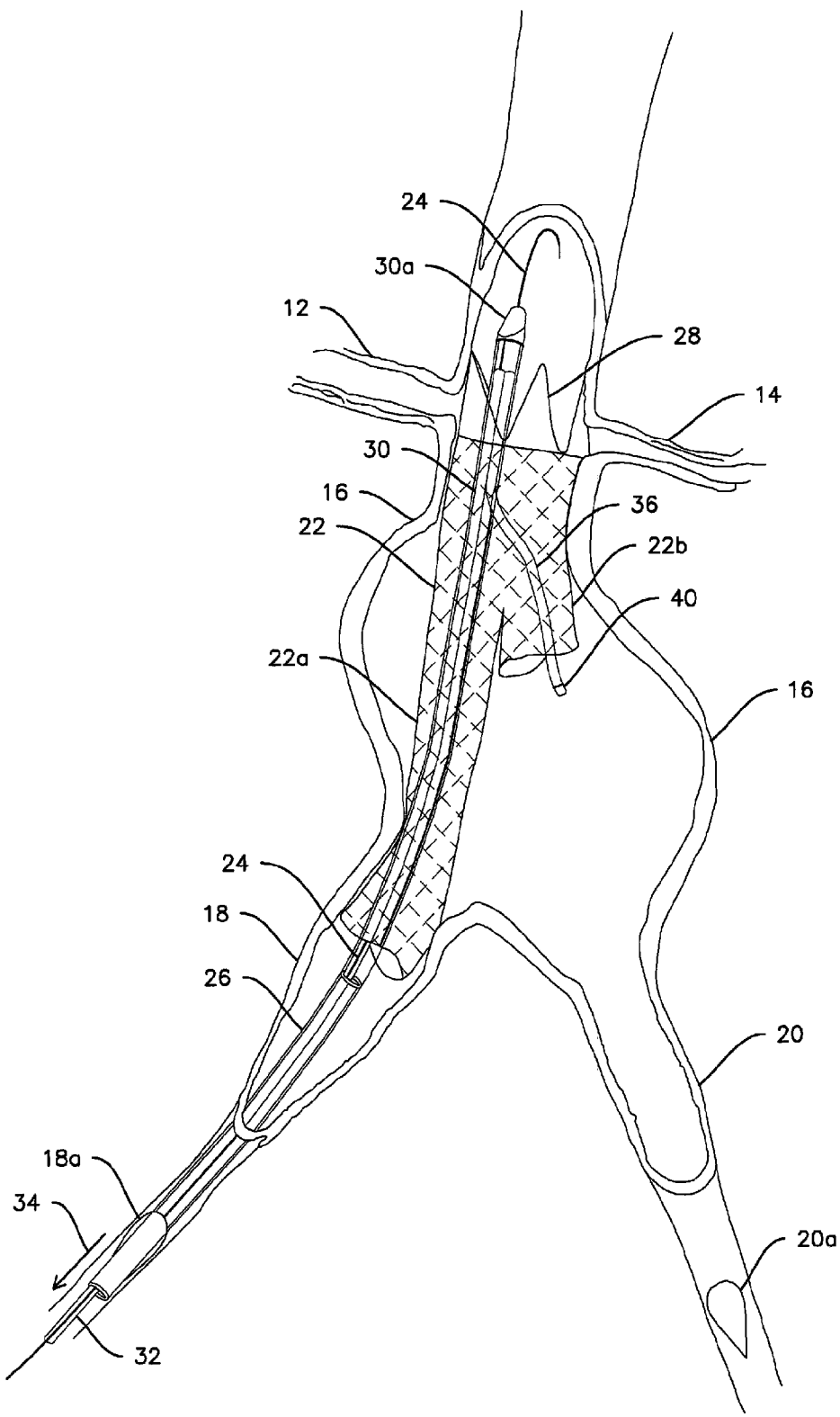
FIG. 4 is the third animation of said series of animations.
Figures 13A, 13B:
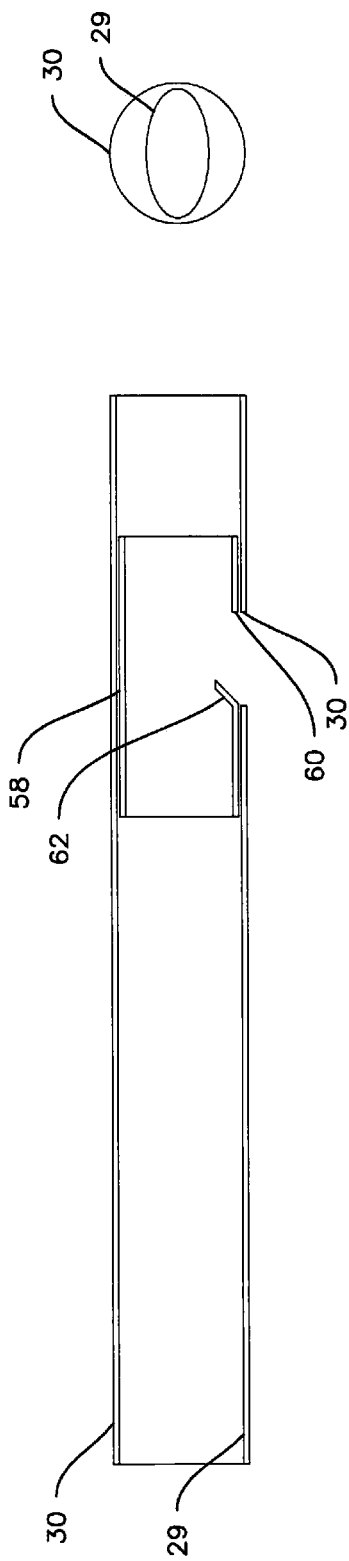
FIG. 13A is a longitudinal sectional view of the main catheter of this invention.
FIG. 13B is an end view of the structure depicted in FIG. 13A.

The lower left corner of FIG. 4 depicts manually pulling inner cannula 32 in the distal-to-proximal direction indicated by directional arrow 34 when the first or second embodiment of inner cannula 32 is used, i.e., both embodiments include extended arm 36. Retraction of inner cannula 32 relative to stationary main catheter 30 therefore enables extended arm 36 (center of FIG. 4) to travel through exit opening 31 formed in main catheter 30. Exit opening 31 and its associated kick plate 62 that guides extended arm 36 out said exit opening is best depicted in FIG. 13A.

Main catheter 30 is then advanced and rotated so that exit opening 31 and therefore extended arm 36 are aligned with but spaced apart from the gate of the stent graft. As is well-known, the gate is located in truncate leg 22b slightly below the flow divider of the stent graft.

When it is clear that extended arm 36 will pass through the gate and enter into the lumen of truncate leg 22b when inner catheter 32 is retracted relative to stationary main catheter 30, i.e., pulled in a distal-to-proximal direction, inner catheter 32 is retracted until the distal end of extended arm 36 is external to truncate limb 22b of main stent graft 22 as depicted in FIG. 4. In a first embodiment of extended arm 36, the free end of extended arm 36 is formed of a ferromagnetic material such as a wire and in a second embodiment, a magnetic tip is secured to said free end when main catheter 30 is manufactured.

Figure 5:
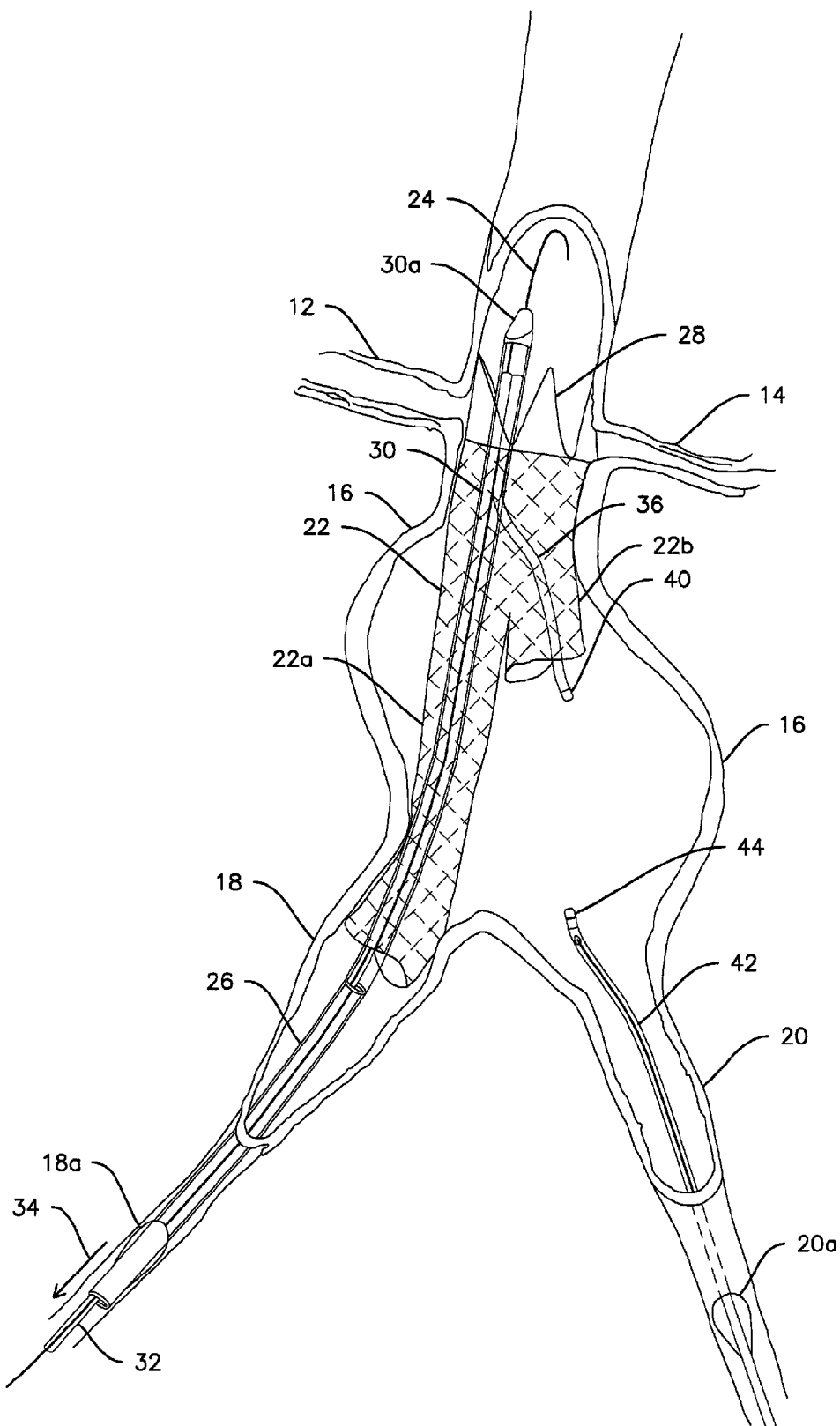
FIG. 5 is the fourth animation of said series of animations.

FIG. 5 depicts the next step of the novel method. Mating catheter 42 is advanced over a guide wire, not depicted, through surgical incision 20a in common iliac artery 20. An introducer sheath, not depicted, smaller in diameter than introducer sheath 26, is also introduced through said incision 20a. The leading end of mating catheter 42 carries magnetic tip 44 which has a magnetic polarity opposite to the magnetic polarity of magnetic tip 40 if the second embodiment of the extended arm is in use.

Figure 6:
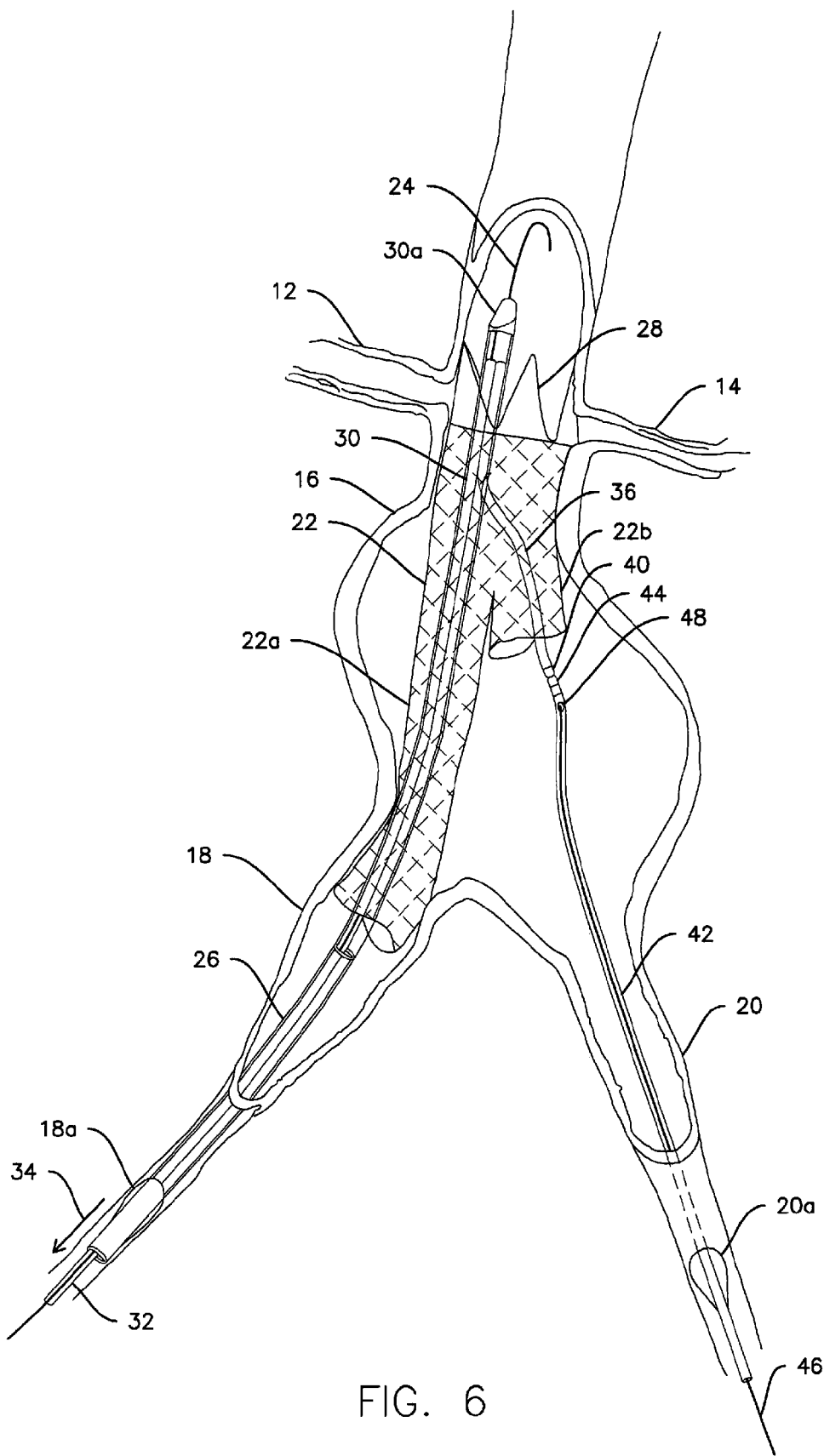
FIG. 6 is the fifth animation of said series of animations.

Mating catheter 42 is then advanced and manipulated until magnetic tip 44 magnetically couples with magnetic tip 40 (or the ferromagnetic wire if the first embodiment of extended arm 36 is used) as illustrated in FIG. 6.

The guide wire referred to but not depicted in connection with FIG. 5 is depicted in the lower right corner of FIG. 6 and is denoted 46. It is hereinafter referred to as the contralateral guide wire. Reference numeral 48 denotes an exit opening formed in mating catheter 42 near its distal end for said contralateral guide wire 46.

Both catheters, i.e., main catheter 30 and mating catheter 42, are advanced together in order to advance contralateral guide wire 46 through exit opening 48 in a proximal-to-distal direction.

Figure 7:
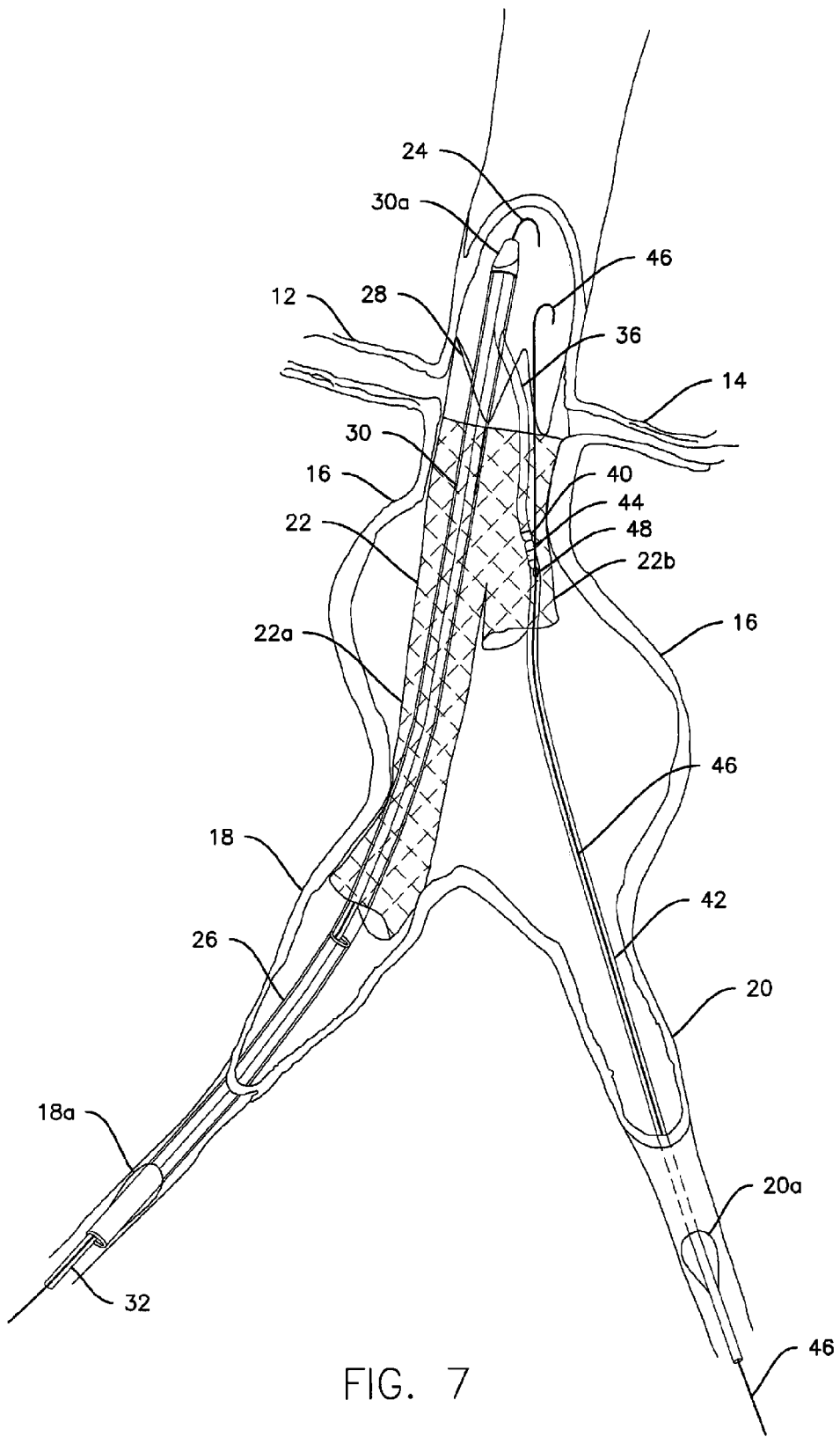
FIG. 7 is the sixth animation of said series of animations.

After contralateral guide wire 46 is successfully extended through exit opening 48, it is extended until it is positioned distal to the distal end of the stent graft, just like the distal end of first guide wire 24, as indicated in said FIG. 7.

Magnetic tips 40 and 44 are then separated from one another.

Figure 8:
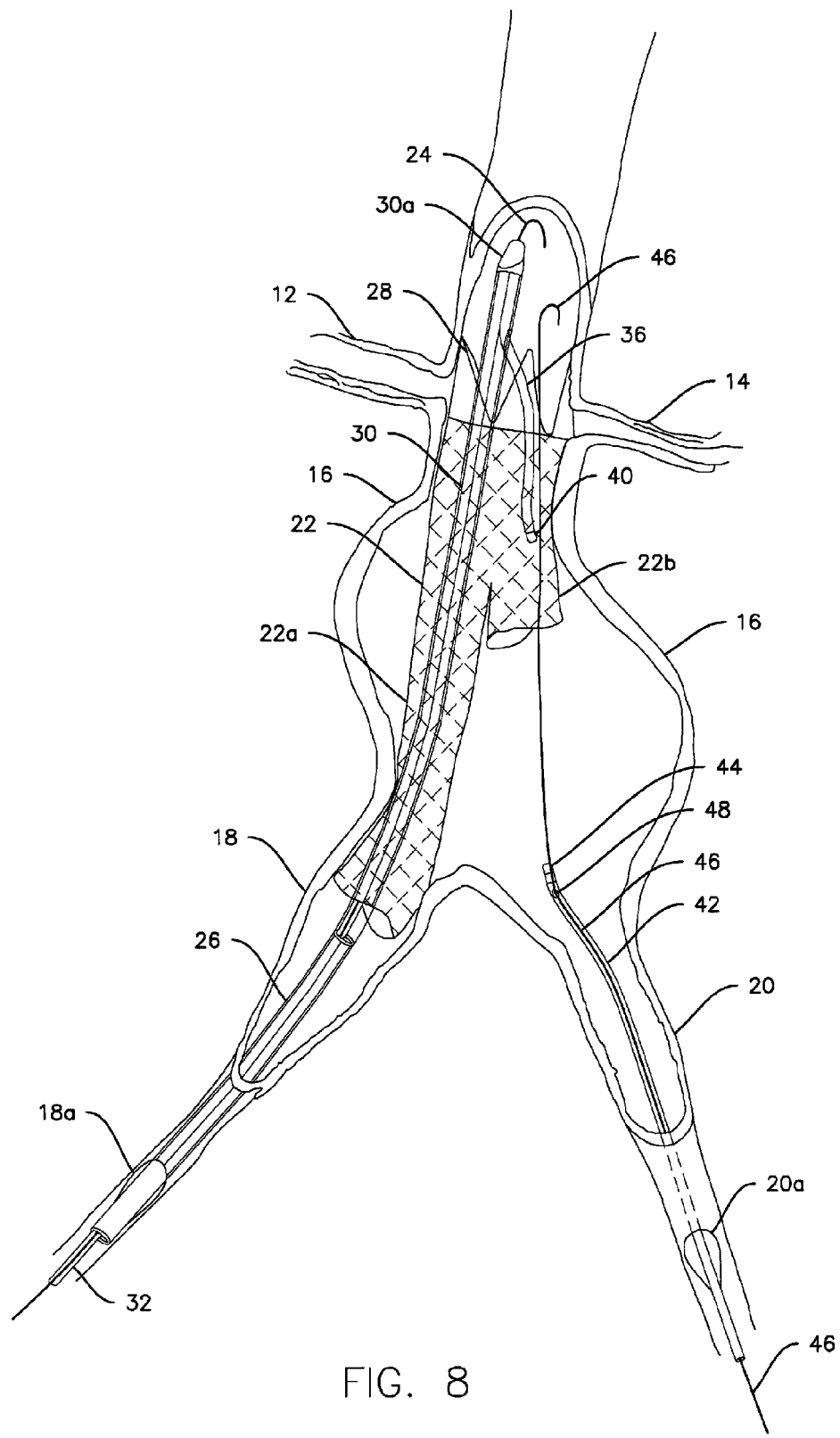
FIG. 8 is the seventh animation of said series of animations.

FIG. 8 depicts the respective positions of the parts after magnetic tips 40 and 44 are decoupled. The separation is accomplished by holding main catheter 30 in a fixed position while pulling on mating catheter 42. Mating catheter 42 is then retracted through contralateral puncture site 20a. Contralateral guide wire 46 is left in place.

Figure 9:
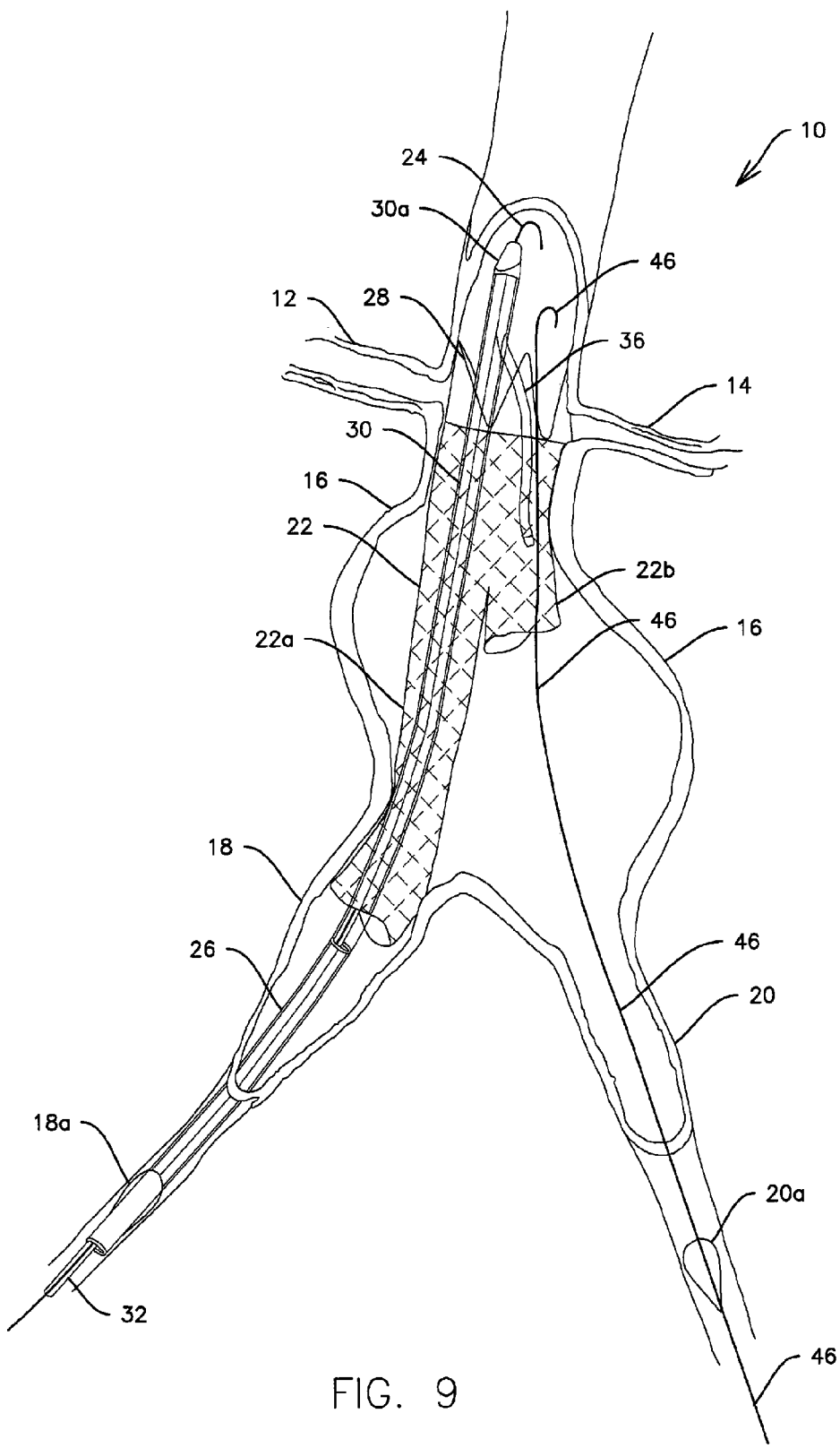
FIG. 9 is the eighth animation of said series of animations.

FIG. 9 depicts contralateral guide wire 46 in its FIG. 8 position, i.e., with mating catheter 42 removed.

Figure 10:
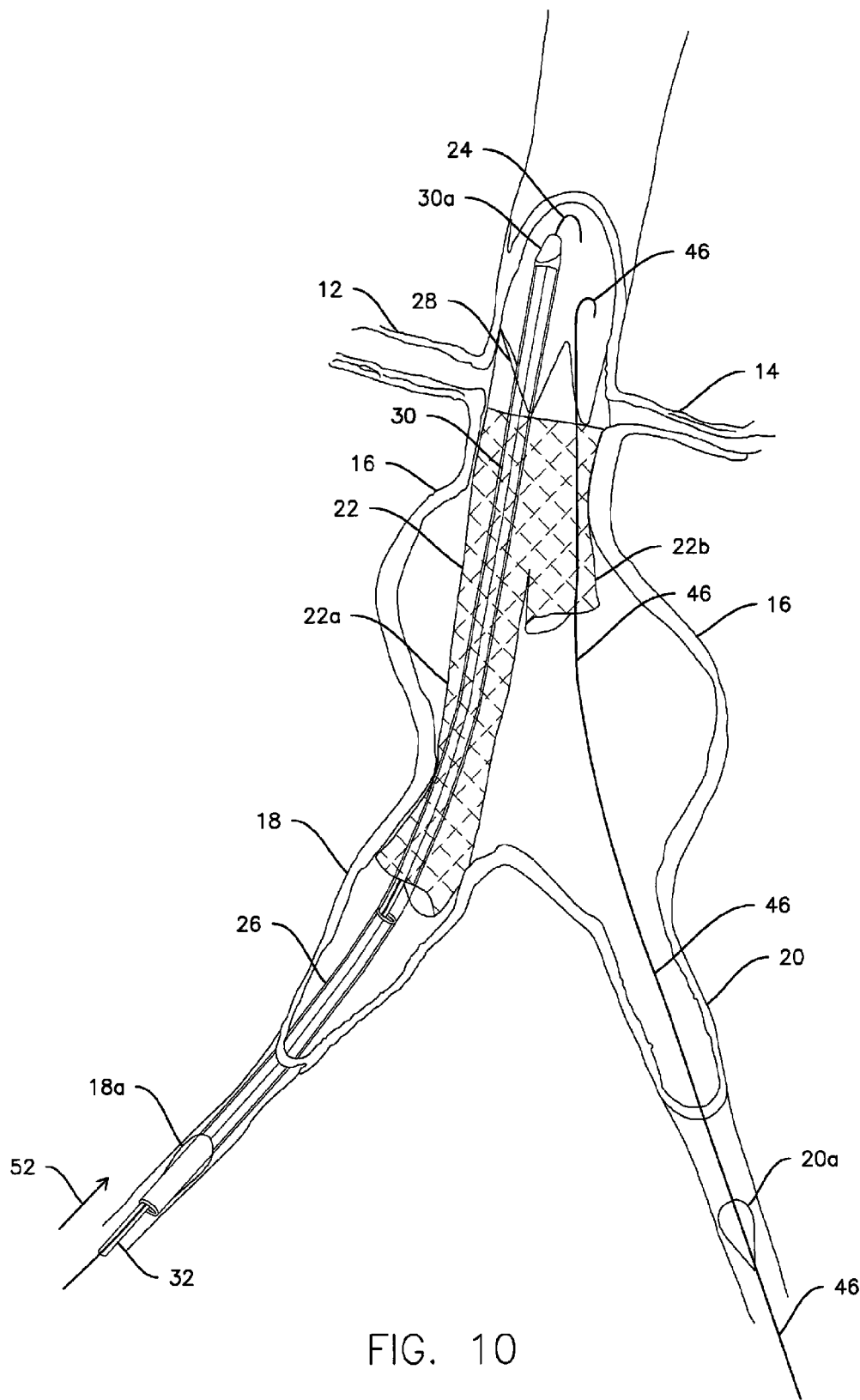
FIG. 10 is the ninth animation of said series of animations.

Inner cannula 32, depicted in the lower left corner of FIG. 10, is then pushed in the proximal-to-distal direction of directional arrow 52 to retrieve extended arm 36 through exit opening 31 into main catheter 30.

Figure 11:
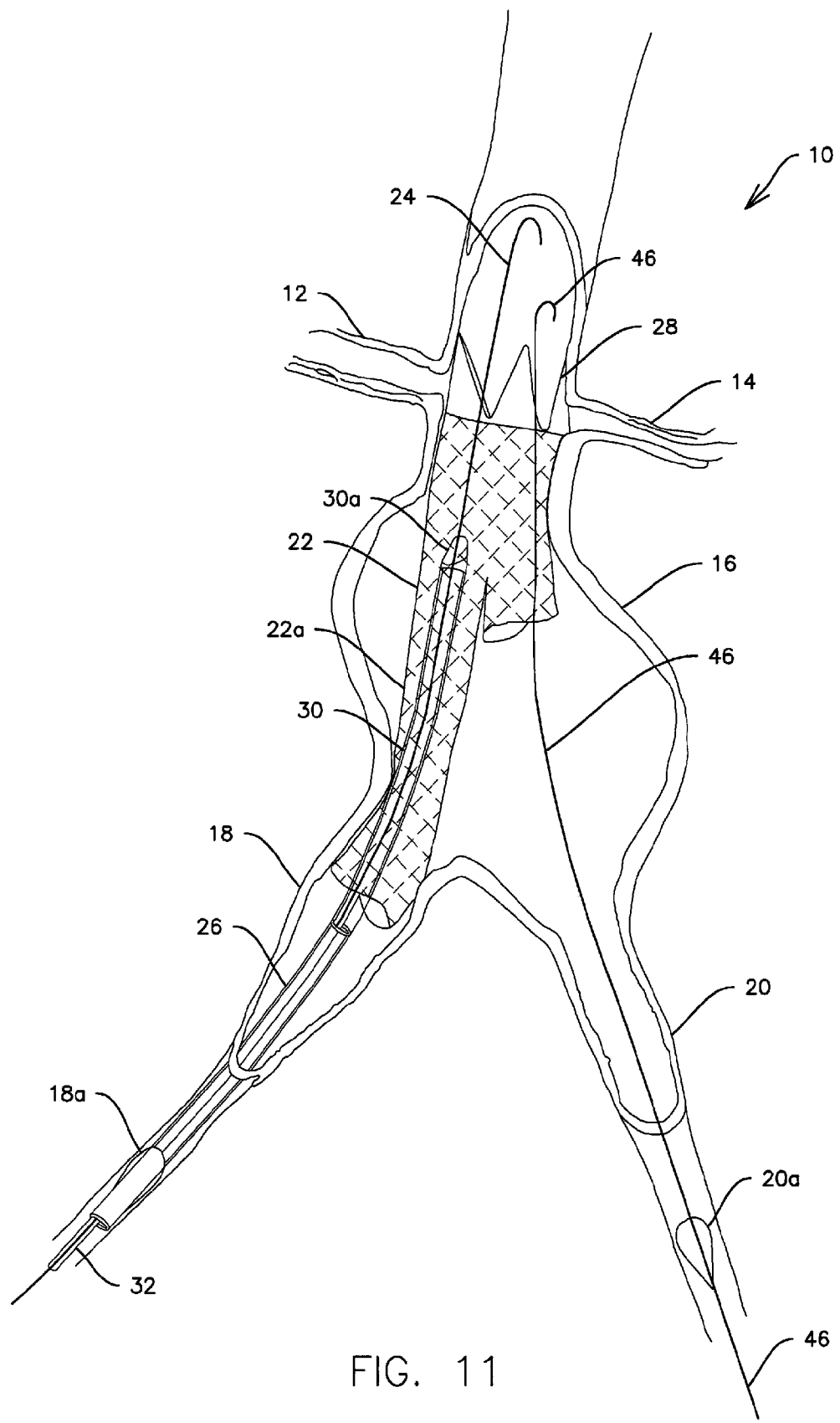
FIG. 11 is the tenth animation of said series of animations.

FIG. 11 depicts withdrawal of main catheter 30 and inner cannula 32, including extended arm 36, through puncture opening 18a in the ipsilateral side of the patient's body.

Figure 12:
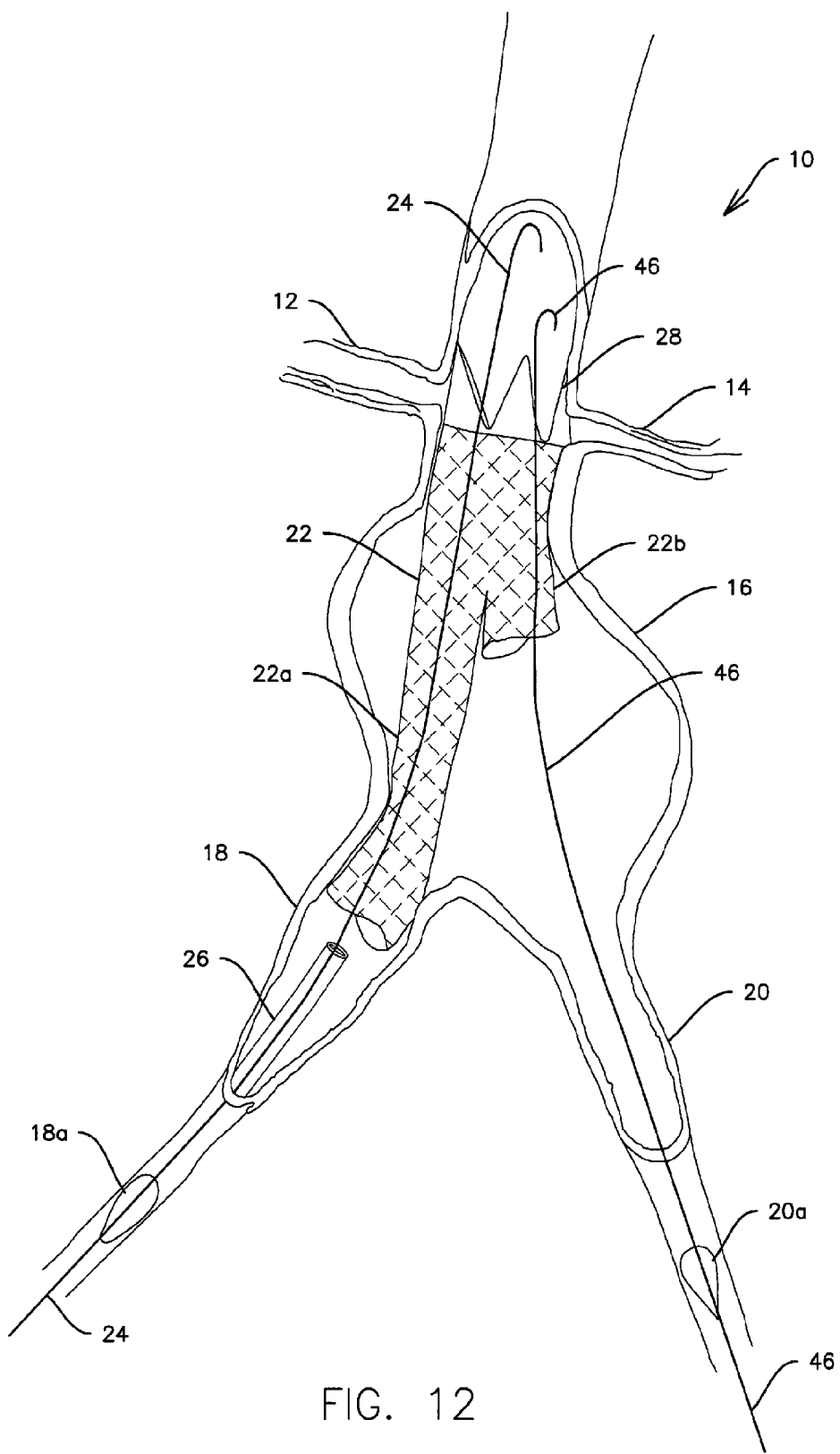
FIG. 12 is the eleventh and final animation of said series of animations.

FIG. 12 depicts site 10 when main catheter 30 is fully withdrawn through puncture opening 18a. Guide wires 24 and 46 remain in their respective FIG. 11 positions. Contralateral guide wire 46 is used to advance the contralateral limb of the stent graft for accurate placement.

FIG. 13A is a longitudinal sectional view of main catheter 30. Exit opening 31 is formed in main catheter 30, said opening being the exit opening for extended arm 36.

Radiopaque ring 58 is also depicted in said FIG. 13A, said radiopaque ring being disposed in lumen 29 of main catheter 30 and having opening 60 that is in registration with exit opening 31. In addition to enhancing the imaging of the novel tool and procedure, radiopaque ring 58 also structurally reinforces main catheter 30 in the region of exit opening 31.

Figure 16:
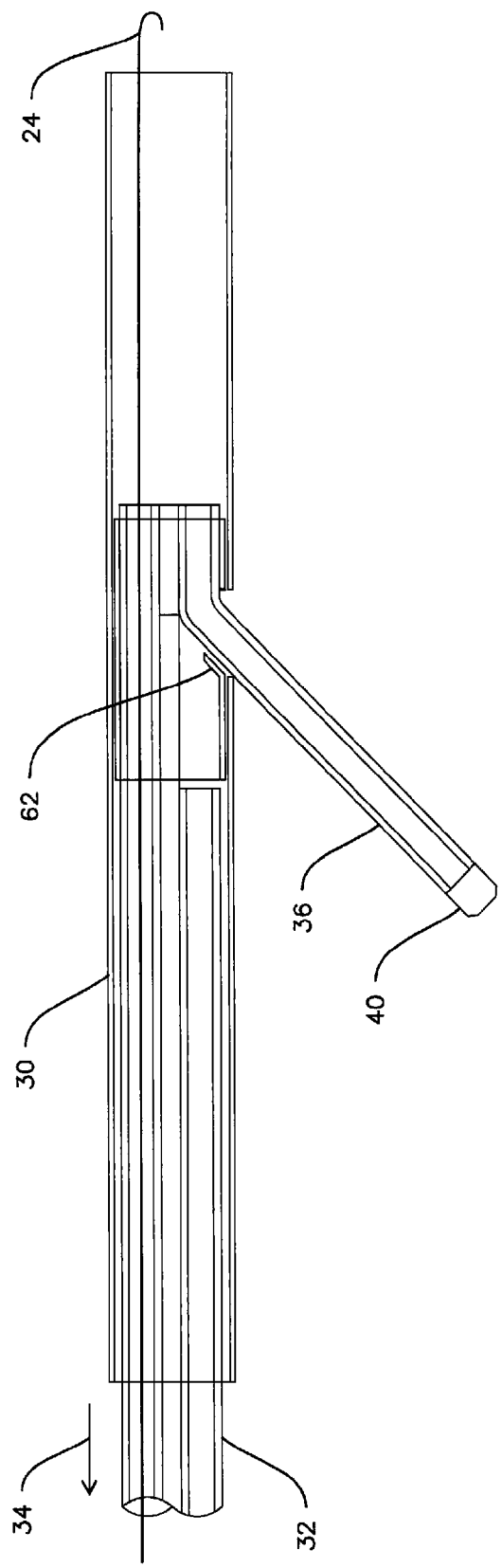
FIG. 16 is a longitudinal sectional view of the structure depicted in FIG. 15 but with the extended arm extending through the exit hole formed in the main catheter.

FIG. 13A also depicts kick plate 62 which is formed in ring 58 and has utility in controlling the angle of exit of extended arm 36 as disclosed more fully in connection with FIG. 16.

FIG. 13B is an end view of main catheter 30. Main catheter 30 has oval lumen 29 to receive inner cannula 32 and to prevent rotation of said inner cannula in said lumen of main catheter 30.

Figure 14B:
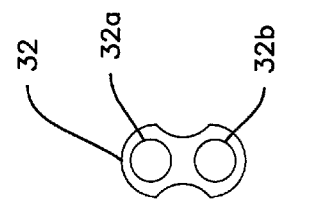
FIG. 14B is an end view of the structure depicted in FIG. 14A.
Figure 14A:
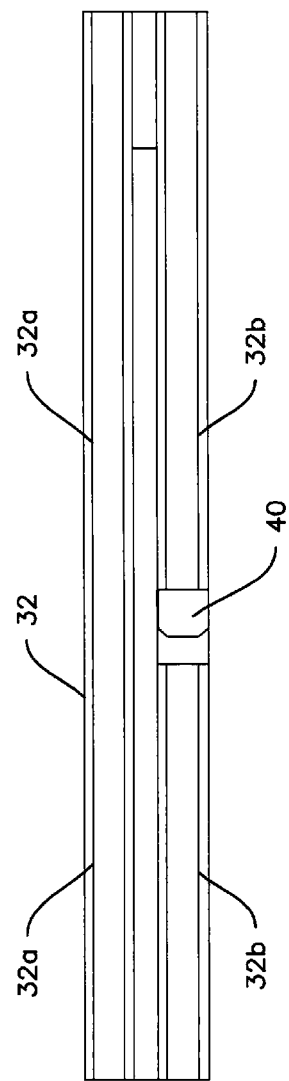
FIG. 14A is a longitudinal sectional view of the inner tubing of this invention.

FIG. 14A is a longitudinal sectional view of inner cannula 32. Inner cannula 32 may be provided in two embodiments as aforesaid, both embodiments having a non-round structure that is prevented from rotation by the mating non-round lumen of main catheter 30.

Figure 15:
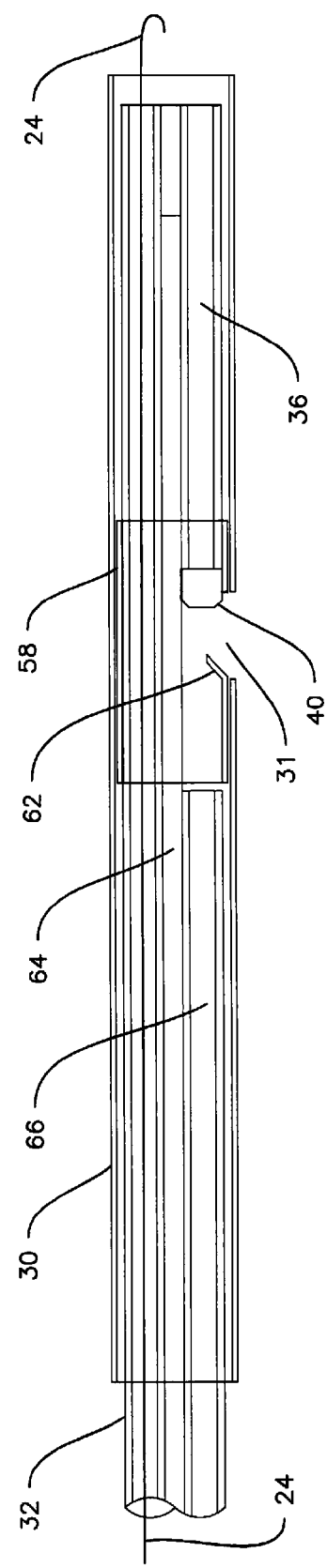
FIG. 15 is a longitudinal sectional view depicting the inner tubing and the extended arm in the lumen of the main catheter.

In both embodiments of inner cannula 32, the first cannula having lumen 32a receives main guide wire 24 as best depicted in FIG. 15 and the second cannula having lumen 32b is cut near its distal end to form extended arm 36, as also best depicted in FIG. 15. In the second embodiment of inner cannula 32, that part of lumen 32b proximal to the cut is removed and discarded as aforesaid. In both embodiments, the first and second inner cannulas are separated from one another for a predetermined extent on the distal end of the cut, remaining connected to one another at their respective distal ends so that extended arm 36 has a free end that extends through exit opening 31 when inner cannula 32 is retracted in a distal-to-proximal direction.

FIG. 15 is a longitudinal sectional view depicting extended arm 36 inside lumen 32b of inner cannula 32. Magnetic tip 40 is in open communication with exit opening 31.

Extended arm 36 and hence magnetic tip 40 have exited exit opening 31 in FIG. 16 because inner cannula 32 has been pulled in the distal-to-proximal direction indicated by directional arrow 34 as disclosed above in connection with FIG. 4. The function of kick plate 62 in controlling the angle of extended arm 36 is made clear by said FIG. 16.

Figure 17:
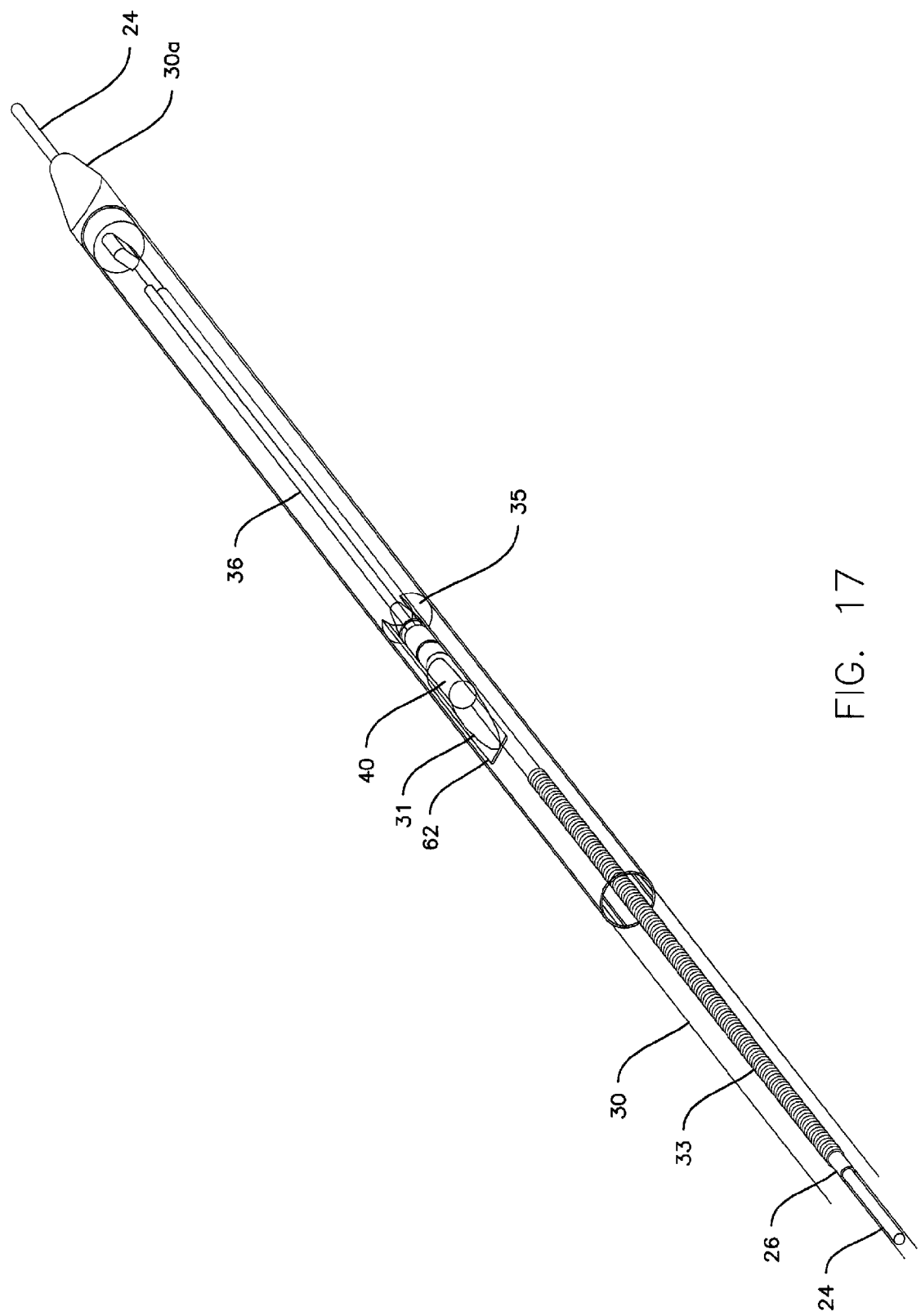
FIG. 17 is a perspective view of an additional embodiment of the main catheter.

In a third embodiment of extended arm 36, depicted in FIG. 17, said extended arm is formed of a nickel-titanium alloy (Nitinol® memory metal) so that its deployed shape can be predetermined at the time of manufacture.

In an additional embodiment of the inventive structure as a whole, also depicted in FIG. 17, stainless steel tubing 33 ensleeves first inner cannula having lumen 32a along a predetermined extent thereof. Stainless steel tubing 33 is positioned in the lumen of main catheter 30 in non-sliding relation thereto. The stainless steel tubing facilitates pushing of the first inner cannula in a proximal-to-distal direction by providing rigidity in the direction of the pushing force. It also facilitates rotation of said first inner cannula and hence of the second inner cannula to which it is connected. However, stainless steel tubing 33 has limited flexibility.

In still another embodiment of the novel structure as a whole, also depicted in FIG. 17, elongate coiled spring 35 ensleeves the first inner cannula along a predetermined extent thereof, said elongate coiled spring being positioned in lumen 29 of main cannula 30. Coiled spring 35 facilitates pushing of the first inner cannula in a proximal-to-distal direction by providing rigidity in the direction of the pushing force and flexibility to negotiate bends or curves within the patient's body. It also facilitates rotation of main catheter 30 and hence of the first and second inner cannulas.

Instead of providing main catheter 30 with an oval or other non-round lumen, a truncate non-rotation catheter 37 may be secured to lumen 29 of main catheter 30 as depicted in FIG. 17. Truncate catheter 37 is cut out or slotted as depicted to receive inner cannula 32 to prevent rotation of said inner cannula relative to said main catheter lumen as said inner cannula is slidingly advanced or retracted within the lumen of the main catheter as the novel method steps are performed.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

What is claimed is:

1. A method for installing a stent graft having an elongate limb and a truncate limb for treatment of an abdominal aortic aneurysm, comprising the steps of:

puncturing a first common iliac artery and advancing a main body of the stent graft over a main body guide wire and a first introducer sheath to deliver and deploy said main body in therapeutic relation to said aneurysm;

providing a main catheter having a lumen and an exit opening, where said lumen slideably receives an inner cannula, wherein said inner cannula includes a first cannula and a second cannula that are secured to one another at their respective distal ends, said second cannula has an extended arm, said extended arm secured to a distal end of said first cannula and unsecured to said first cannula proximal to said distal end a ferromagnetic material is mounted to a free end of said extended arm, said first cannula is adapted to slideably receive said main body guide wire;

advancing said main catheter over said main body guide wire and said first introducer sheath in a proximal-to-distal direction until a distal, leading end of said main catheter is positioned distal to a distal end of said stent graft; and manually pulling said inner cannula in a distal-to-proximal direction to cause the extended arm to exit the exit opening formed in said main catheter.

2. The method of claim 1, further comprising the steps of:

rotating said main catheter so that said exit opening and said extended arm are aligned with a gate area of said stent graft.

3. The method of claim 2, further comprising the steps of:

manipulating said main catheter until said distal end and said free end of said extended arm are external to said truncate limb on a proximal end thereof.

4. The method of claim 3, further comprising the steps of:

providing a mating catheter having an exit opening formed therein near a distal end thereof a magnetic tip secured to said distal end of said mating catheter; providing a second introducer sheath that is smaller in diameter than said first introducer sheath; puncturing a second common iliac artery and advancing said mating catheter over a contralateral guide wire;

advancing said mating catheter and manipulating said mating catheter until the magnetic tip of said mating catheter magnetically couples with the ferromagnetic free end of the extended arm.

5. The method of claim 4, further comprising the steps of:

advancing said main catheter and said mating catheter together in a proximal-to-distal direction in order to advance said contralateral guide wire through the exit opening formed in said mating catheter;

continuing said advancing of said main catheter and said mating catheter until a distal end of said contralateral guide wire is distal to the distal end of the stent graft.

6. The method of claim 5, further comprising the steps of:

decoupling said magnetic tip of said mating catheter from the ferromagnetic free end of said extended arm by holding said main catheter in a fixed position while pulling on said mating catheter in a distal-to-proximal direction; and retracting said mating catheter through said second iliac puncture site, leaving said contralateral guide wire in place.

7. The method of claim 6, further comprising the steps of:

pushing said inner cannula in a proximal-to-distal direction to retrieve said extended arm into said main catheter through said exit opening formed in said main catheter;

withdrawing in a distal-to-proximal direction said main catheter through the puncture opening formed in the first common iliac artery, leaving said main catheter guide wire; and advancing said contralateral guide wire to advance a contralateral limb of said stent graft for accurate placement.

8. The method of claim 7, a magnetic tip having a polarity opposite to a polarity of said mating catheter magnetic tip secured to a free end of said extended arm.

9. The method of claim 8, further comprising the steps of: providing a kick plate as a part of said radiopaque ring and positioning said kick plate on a proximal end of said exit opening to control an angle of exit of said extended arm when said inner cannula is pulled in said distal-to-proximal direction.

10. The method of claim 7, a radiopaque ring positioned in the lumen of said main catheter, an opening in said radiopaque ring that is in registration with the exit opening formed in said main catheter, said radiopaque ring enhancing the imaging of the guide wires, catheters and introducer sheaths used in said method and said radiopaque ring structurally reinforcing said main catheter in the region of said main catheter exit opening.

11. The method of claim 10, said main catheter having a circular exterior surface and a non-round lumen to prevent rotation of said inner cannula within said lumen of said main catheter.

12. The method of claim 1, said first and second cannulas being secured to one another along their respective lengths proximal to said respective distal ends.

13. The method of claim 12, said second cannula cut at a location proximal to said distal end of said second cannula said extended arm formed by separating said second cannula from said first cannula along an extent thereof that is distal to said cut and proximal to said distal end of said second cannula.

14. The method of claim 12, said first cannula ensleeved within the lumen of a stainless steel tubing to facilitate displacement of said first cannula in a proximal-to-distal direction.

15. The method of claim 12, said first cannula ensleeved within the lumen of an elongate coiled spring to facilitate displacement of said first cannula in a proximal-to-distal direction and to facilitate bending of said first cannula.

16. The method of claim 1, said first and second cannulas formed independently so that they are connected to one another only at their respective distal ends; and cutting said second cannula at a location proximal to said distal end of said second cannula.

17. The method of claim 16, said first cannula ensleeved within the lumen of a stainless steel tubing to facilitate displacement of said first cannula in a proximal-to-distal direction; and a distal end of said stainless steel tubing ensleeved within a lumen of said main catheter in non-sliding relation thereto so that displacement of said stainless steel tubing effects simultaneous and corresponding displacement of said main catheter.

18. The method of claim 16, said first cannula ensleeved within the lumen of an elongate coiled spring to facilitate displacement of said first cannula in a proximal-to-distal direction and to facilitate bending of said first cannula; and a distal end of said elongate coiled spring ensleeved within a lumen of said main catheter in non-sliding relation thereto so that displacement of said elongate coiled spring effects simultaneous and corresponding displacement of said main catheter.

* * * * *